(12) United States Patent
Hur et al.

(10) Patent No.: US 10,888,721 B2
(45) Date of Patent: Jan. 12, 2021

(54) BREATH RESPONSIVE POWERED AIR PURIFYING RESPIRATOR

(71) Applicant: Design West Technologies, Inc., Tustin, CA (US)

(72) Inventors: Ryan Hur, Irvine, CA (US); Dennis Grudt, Tustin, CA (US); Bob Olson, Huntington Beach, CA (US); Jeffrey Kim, Irvine, CA (US); Ramesh Palanisamy, Riverside, CA (US)

(73) Assignee: Design West Technologies, Inc., Tustin, CA (US)

( * ) Notice: Subject to any disclaimer, the term of this patent is extended or adjusted under 35 U.S.C. 154(b) by 438 days.

(21) Appl. No.: 15/663,599

(22) Filed: Jul. 28, 2017

(65) Prior Publication Data

US 2018/0028846 A1 Feb. 1, 2018

Related U.S. Application Data

(60) Provisional application No. 62/368,075, filed on Jul. 28, 2016.

(51) Int. Cl.
*A61M 16/00* (2006.01)
*A62B 23/02* (2006.01)
(Continued)

(52) U.S. Cl.
CPC ......... *A62B 19/00* (2013.01); *A61M 16/0003* (2014.02); *A61M 16/0051* (2013.01);
(Continued)

(58) Field of Classification Search
CPC .......... A61M 16/0003; A61M 16/0051; A61M 16/0069; A61M 2205/8206; A62B 17/04;
(Continued)

(56) References Cited

U.S. PATENT DOCUMENTS 1,691,648 A * 11/1928 Drager ................... A62B 18/00
128/205.27
2,130,555 A * 9/1938 Malcom ................. A62B 23/02
55/377
(Continued)

FOREIGN PATENT DOCUMENTS

CN 106075760 A 11/2016
DE 4202025 A1 7/1993

*Primary Examiner* — Michael J Tsai
*Assistant Examiner* — Nathan M Le
(74) *Attorney, Agent, or Firm* — Inskeep IP Group, Inc.

(57) ABSTRACT

An air purifying respirator includes a dual stage fan that sucks outside air in through the filter canisters and then pushes the filtered air on to the user's mask or hood, where excess air escapes. A differential pressure sensor measures the pressure within the passages after the dual stage fan and in the ambient environment to estimate the user's rate of respiration. The microcontroller monitors the estimated rate of respiration, as well as the estimated altitude and its estimated amount of oxygen to calculate a user's filtered air flow need. The microcontroller adjusts the van via a fan controller to the appropriate air flow level. The microcontroller further monitors the battery level, filter life, and for low pressure within the user's mask and operates their respective indicators when problem levels arise. The battery supplies power to the microcontroller, power on/off button, and the dual stage fan.

13 Claims, 16 Drawing Sheets

(51) Int. Cl.
  *B01D 46/52* (2006.01)
  *B01D 39/20* (2006.01)
  *B01D 46/24* (2006.01)
  *A62B 18/00* (2006.01)
  *A62B 18/08* (2006.01)
  *A62B 9/00* (2006.01)
  *A62B 19/00* (2006.01)
  *A62B 17/04* (2006.01)
  *B01D 46/00* (2006.01)

(52) U.S. Cl.
  CPC ......... *A61M 16/0069* (2014.02); *A62B 9/006* (2013.01); *A62B 17/04* (2013.01); *A62B 18/006* (2013.01); *A62B 18/088* (2013.01); *A62B 23/02* (2013.01); *B01D 39/2017* (2013.01); *B01D 46/0036* (2013.01); *B01D 46/2411* (2013.01); *B01D 46/521* (2013.01); *A61M 2205/8206* (2013.01); *B01D 2279/40* (2013.01)

(58) Field of Classification Search
  CPC ..... A62B 18/006; A62B 18/088; A62B 19/00; A62B 23/02; A62B 9/006; B01D 2279/40; B01D 39/2017; B01D 46/0036; B01D 46/2411; B01D 46/521
  See application file for complete search history.

(56) References Cited

U.S. PATENT DOCUMENTS

| | | | | |
|---|---|---|---|---|
| 3,864,109 | A * | 2/1975 | Hansen | B01D 46/0004 55/324 |
| 4,264,936 | A * | 4/1981 | Mosciatti | G11B 15/58 226/95 |
| 5,413,097 | A * | 5/1995 | Birenheide | A62B 7/10 128/202.22 |
| 5,735,452 | A | 4/1998 | Yu et al. | |
| 5,906,203 | A * | 5/1999 | Klockseth | A62B 18/006 128/201.25 |
| 5,950,621 | A * | 9/1999 | Klockseth | A62B 9/006 128/204.26 |
| 6,146,449 | A * | 11/2000 | Lee | B01D 46/0001 128/206.17 |
| 6,149,700 | A * | 11/2000 | Morgan | B01D 46/2414 123/198 E |
| 6,152,996 | A * | 11/2000 | Linnersten | B01D 46/0024 55/385.3 |
| 6,761,162 | B1 * | 7/2004 | Swann | A62B 17/04 128/201.25 |
| 6,874,499 | B2 | 4/2005 | Viner et al. | |
| 6,933,277 | B2 | 8/2005 | Brenneman et al. | |
| 6,953,318 | B2 * | 10/2005 | Krugerke | A62B 18/006 128/201.29 |
| 7,118,608 | B2 | 10/2006 | Lovell | |
| 7,331,686 | B2 | 2/2008 | Ossevoort et al. | |
| 7,479,079 | B2 | 1/2009 | Takeda et al. | |
| 7,538,036 | B2 | 5/2009 | Busch et al. | |
| 7,748,380 | B1 * | 7/2010 | Phifer | A62B 7/02 128/201.25 |
| 7,841,706 | B2 | 11/2010 | Ishinaga et al. | |
| 8,098,792 | B2 | 1/2012 | Hsu et al. | |
| 8,361,181 | B2 * | 1/2013 | Osendorf | B01D 46/0004 55/476 |
| 9,003,357 | B1 | 4/2015 | Andrade et al. | |
| 2004/0025880 | A1 * | 2/2004 | Capon | A62B 9/04 128/206.15 |
| 2004/0134171 | A1 * | 7/2004 | Scott | B01D 46/0001 55/482 |
| 2004/0226563 | A1 * | 11/2004 | Xu | A62B 18/02 128/206.21 |
| 2005/0102986 | A1 * | 5/2005 | Gosweiler | B01D 46/0058 55/502 |
| 2005/0155665 | A1 * | 7/2005 | Schlacchter | A62B 23/02 141/12 |
| 2005/0223902 | A1 * | 10/2005 | Lovell | B01D 53/0415 96/134 |
| 2005/0247310 | A1 * | 11/2005 | Grove | A62B 17/04 128/201.22 |
| 2006/0174874 | A1 * | 8/2006 | Jagger | A61M 16/10 128/201.21 |
| 2007/0240716 | A1 * | 10/2007 | Marx | A62B 18/006 128/204.21 |
| 2008/0041026 | A1 * | 2/2008 | Engel | B01D 46/2411 55/432 |
| 2008/0066435 | A1 * | 3/2008 | Engel | B01D 46/0004 55/492 |
| 2008/0101966 | A1 * | 5/2008 | Lopatinsky | F04D 25/0653 417/423.4 |
| 2009/0183636 | A1 * | 7/2009 | Levine | B01D 46/10 96/397 |
| 2009/0266361 | A1 * | 10/2009 | Bilger | A62B 7/10 128/204.21 |
| 2010/0145211 | A1 * | 6/2010 | Yamamori | A61B 5/0878 600/538 |
| 2010/0224190 | A1 * | 9/2010 | Tilley | A62B 18/006 128/204.21 |
| 2011/0056496 | A1 * | 3/2011 | Tilley | A62B 7/10 128/205.27 |
| 2011/0126828 | A1 * | 6/2011 | Wu | A62B 7/10 128/201.25 |
| 2011/0162644 | A1 * | 7/2011 | Ujhazy | A61M 16/0069 128/203.12 |
| 2012/0055126 | A1 * | 3/2012 | Whittier | B01D 46/0024 55/414 |
| 2012/0085349 | A1 * | 4/2012 | Tobias | A62B 9/006 128/204.22 |
| 2012/0160755 | A1 * | 6/2012 | LaCroix | B01D 29/21 210/232 |
| 2013/0014752 | A1 * | 1/2013 | Ausen | A62B 7/10 128/201.25 |
| 2013/0146052 | A1 * | 6/2013 | Ding | A62B 7/10 128/202.22 |
| 2013/0174845 | A1 * | 7/2013 | Vinnakota | A62B 9/006 128/204.22 |
| 2013/0233783 | A1 * | 9/2013 | Schmitt | B01D 29/23 210/234 |
| 2013/0319408 | A1 * | 12/2013 | Zwolinsky | A61M 16/06 128/202.22 |
| 2014/0166001 | A1 * | 6/2014 | Kooken | A62B 23/02 128/201.25 |
| 2014/0238243 | A1 * | 8/2014 | Jardine | B01D 46/0047 96/142 |
| 2015/0020807 | A1 * | 1/2015 | Kimmel | A61M 16/0875 128/204.21 |
| 2015/0176545 | A1 * | 6/2015 | Troxell | F02M 35/086 55/302 |
| 2015/0314225 | A1 * | 11/2015 | Parsons | B01D 35/306 210/237 |
| 2016/0059049 | A1 * | 3/2016 | Langford | A62B 18/08 128/205.27 |
| 2016/0074683 | A1 * | 3/2016 | Bergeron | A62B 18/08 128/201.19 |
| 2016/0074801 | A1 * | 3/2016 | Francis | B01D 46/2411 55/485 |
| 2017/0189727 | A1 * | 7/2017 | Hunter | A62B 18/02 |
| 2017/0363111 | A1 * | 12/2017 | Hur | B01D 46/403 |

* cited by examiner

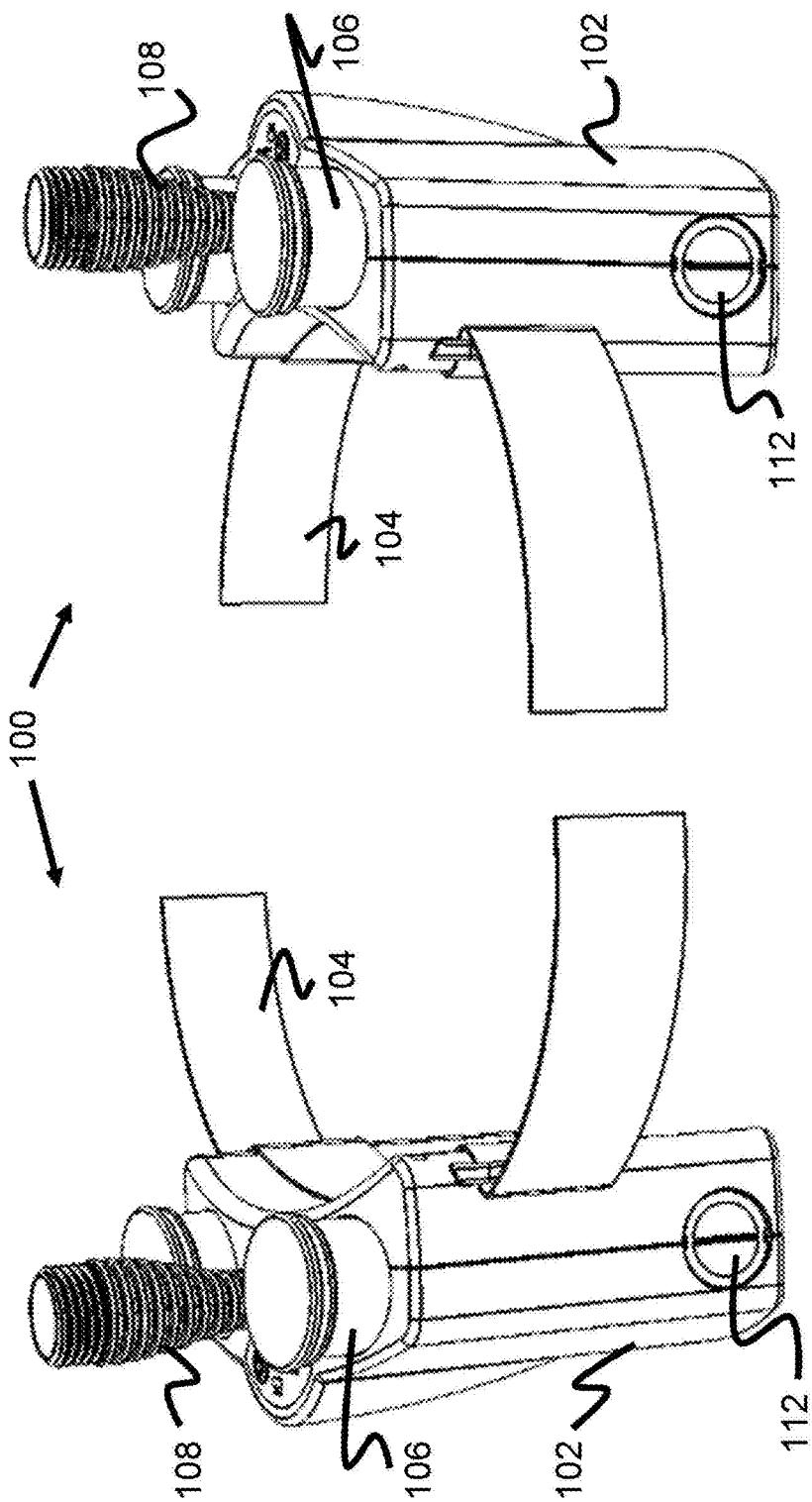

BREATH RESPONSIVE POWERED AIR PURIFYING RESPIRATOR

RELATED APPLICATIONS

This application claims priority to U.S. Provisional Application Ser. No. 62/368,075 filed Jul. 28, 2016 entitled Breath Responsive Powered Air Purifying Respirator, which is hereby incorporated herein by reference in its entirety.

BACKGROUND OF THE INVENTION

The present invention is directed to a novel method of efficient, low power air filtration for Chemical, Biological, Radiation and Nuclear (CBRN) applications that can be used to filter the air for a single user to provide individual protection. Specifically, protection can be provided using a Powered Air Purifying Respirator (PAPR), thereby protecting the user against chemical warfare agents (CWAs) and toxic industrial chemicals (TICs) in the form of dust, mist, and gas.

The PAPR blower is a motorized system which draws air through canisters containing particulate and gas filters. Most commercially available PAPR units supply air exceeding the user demand, at a constant flow and positive pressure, while the unused air is vented through exhaust vent valves in the facemask. While acceptable, these prior art PAPR blowers cycle more air through their systems than necessary, which results in relatively frequent filter canister and battery changes.

SUMMARY OF THE INVENTION

The present invention is directed to a breath-responsive PAPR system, including a fan blower assembly (FBA) for PAPR applications that draws contaminated air through the rain-protected filter canister from the top of the unit and supplies purified air through the breathing tube. The 40 mm outlet tube adapter of the fan blower assembly offers design flexibility to couple with a NIOSH approved face mask or hood.

A dual stage fan sucks outside air in through the filter canisters and then push the filtered air on to the user's mask or hood, where excess air escapes. A differential pressure sensor measures the pressure within the passages after the dual stage fan and in the ambient environment to estimate the user's rate of respiration. The microcontroller monitors the estimated rate of respiration, as well as the estimated altitude and its estimated amount of oxygen to calculate a user's filtered air flow need. The microcontroller adjusts the van via a fan controller to the appropriate air flow level. The microcontroller further monitors the battery level, filter life, and for low pressure within the user's mask and operates their respective indicators when problem levels arise. The battery supplies power to the microcontroller, power on/off button, and the dual stage fan.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 3 is a side view of a respirator system according to the present invention.

FIG. 4 is a side view of a respirator system according to the present invention.

DESCRIPTION OF EMBODIMENTS

Figure 1:
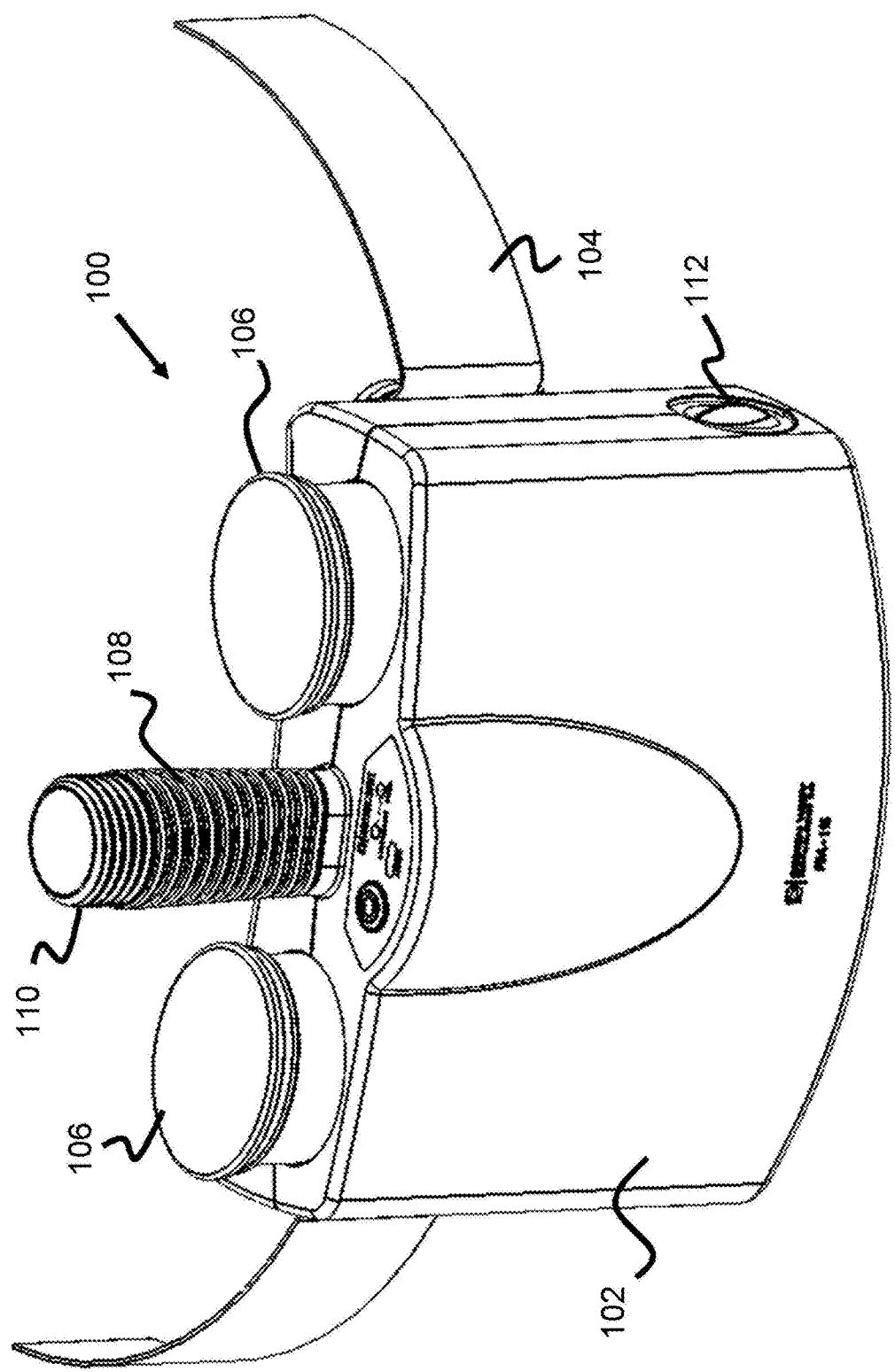
FIG. 1 is a perspective view of a respirator system according to the present invention.
Figure 2:
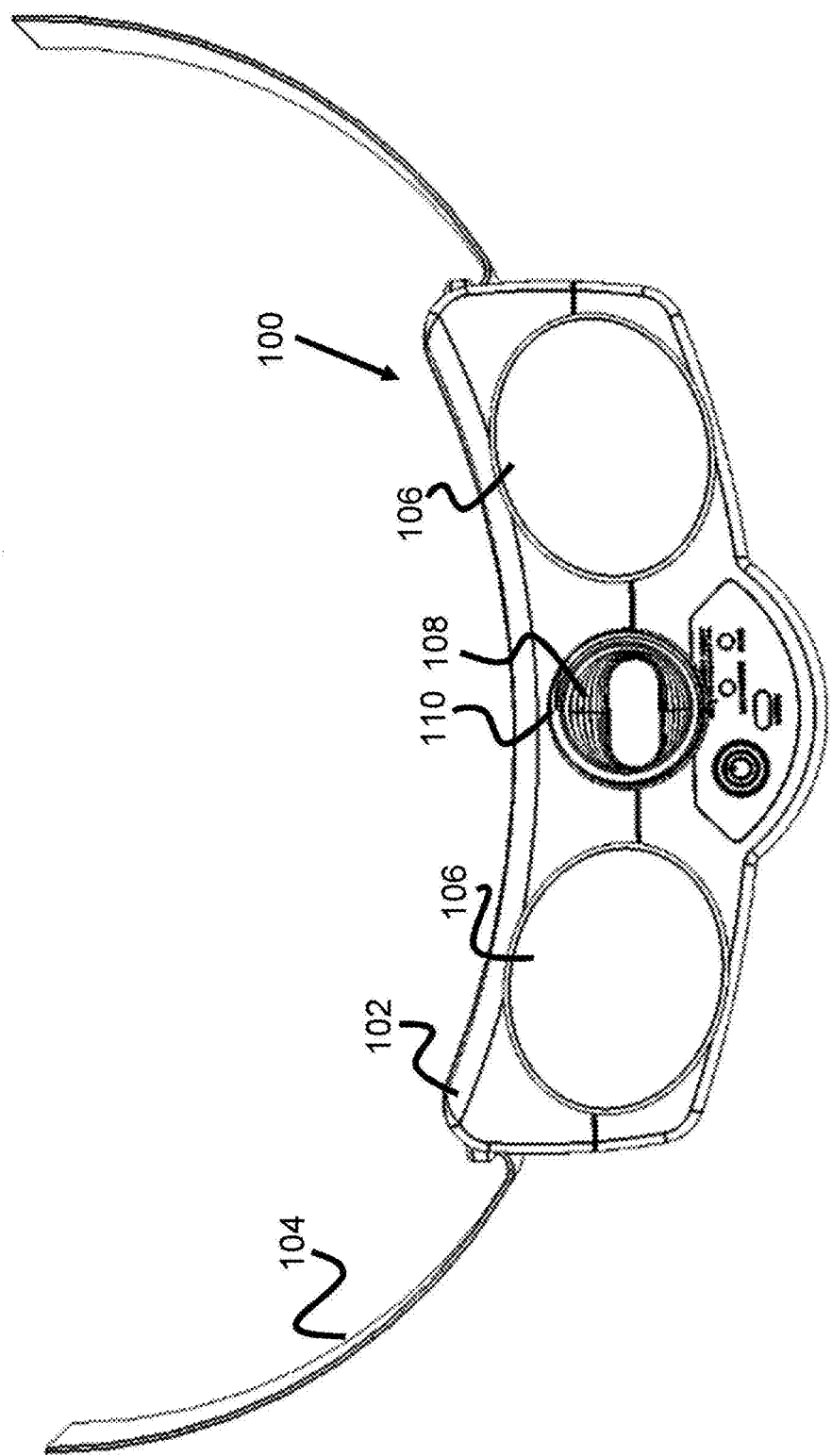
FIG. 2 is a top view of a respirator system according to the present invention.
Figure 5:
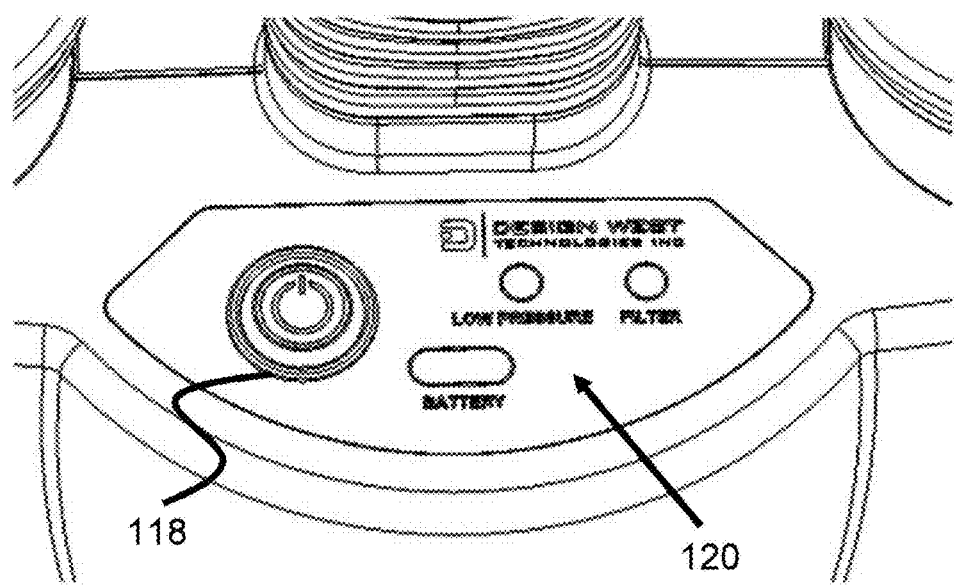
FIG. 5 is a view of an interface for a respirator system according to the present invention.
Figure 6:
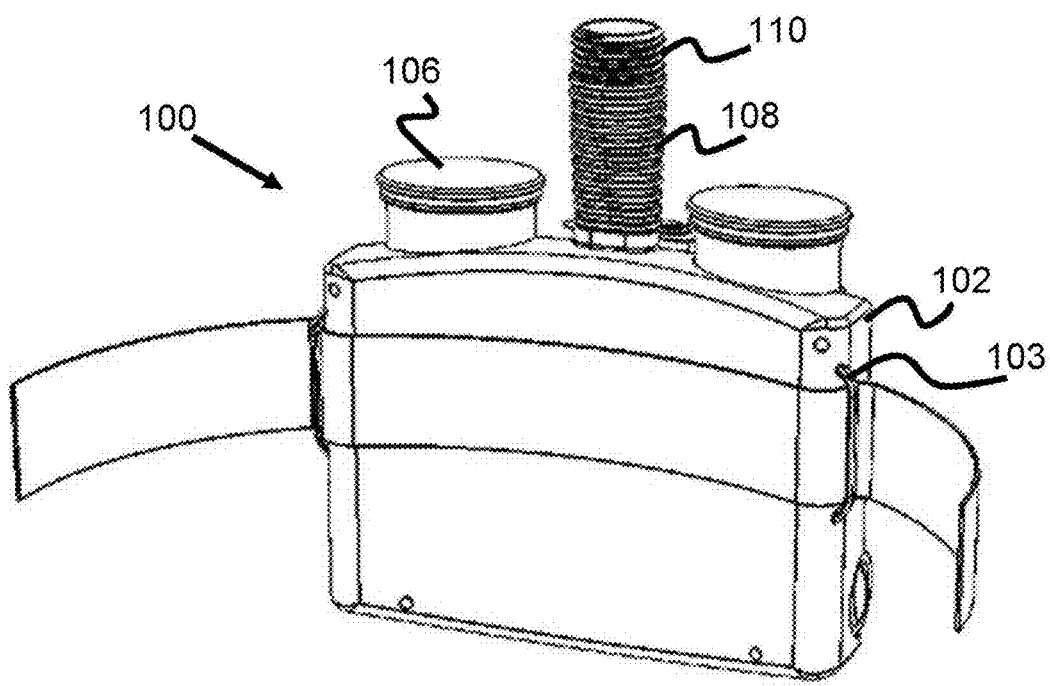
FIG. 6 is a back view of a respirator system according to the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

FIGS. 1-17 illustrate various aspects of a Powered Air Purifying Respirator (PAPR) that can be used for filtration of chemical, biological, radiation, and Nuclear applications (CBRN). As described in more detail below, the respirator system 100 provides improved efficiency, low power use, and improved safety features over prior designs.

As seen best in FIGS. 1-6, the respirator system 100 includes an outer enclosure or housing 102 with a hose adaptor tube 108 and hose connector 110 that outputs filtered air to a user breathing enclosure such as a connected mask or hood. Preferably, the tube 108 and connector 110 are sized and configured to connect to standard commercial tube sizes, such as a 40-mm diameter tube size that couples with a NIOSH approved face mask or hood. A belt 104 is connected via belt loops 103 so that the user can secure the respirator around their torso.

The housing 102 of the respirator system 100 includes top apertures into which filter cartridges 106 slide into to filter the air. As best seen in FIGS. 13-17, each filter cartridge includes an outer cartridge enclosure 106A having an oval cross sectional shape. Air enters the filter cartridge 106 through a space 106C between a top of the enclosure 106C and a top cover 106B, then through opening 106E. In this respect, the cover 106B generally prevents rain and dirt from entering into the filter cartridge 106.

Next, the air moves into the tubular center passage 106F which extends to nearly the bottom of the cartridge 106. The passage 106F includes a plurality of openings that further allow the air to move radially outwards into a first tubular filter 146 and then into a second tubular filter 148. Finally, the air moves downward and out of bottom openings 106D.

In one embodiment, the first tubular filter 146 is a HEPA filter and the second tubular filter 148 is an activated carbon bed. The HEPA filter acts as the first stage, during which aerosol particles as small as 0.3 microns are trapped with about 99.7% efficiency. For example, the HEPA filter can be composed of a pleated glass fiber mat. The pleats help maximize surface area while optimizing airflow resistance, which increases the power draw and battery life of the respirator system 100.

The activated carbon removes the chemical contaminants. Specifically, the impregnated materials on the filtration media either absorbs the agents physically, or breaks down their molecular structure by reacting with them. On example activated carbon material is ASZM-TEDA. Additionally, Universal First Responder (UFR) carbon can be further added to effectively remove TICs, including ammonia.

The relatively tall, cylindrical design of the cartridge 106 and filters 146, 148 provide relatively high surface area and thereby maximizes or otherwise extends the lifetime of the cartridge 106 in contaminated environments. For example, the cartridge 106 has dimensions of about 4.88 inches in length and 2.57 inches in width, leading to about 25% more surface area than a standard C1 Cap 1 filter, resulting in a low airflow resistance throughout the filter and thereby increasing battery run time.

As best seen in FIGS. 6-9 and 18 which show the respirator system 100 with portions of the outer housing 102 removed, the filters cartridges 106 slide into oval tubes 126 that have a diameter slightly larger than the outer diameter of the cartridge 106. This allows the cartridges 106 to snuggly and securely slide into the respirator system 100.

The bottom tubular portion 128 houses a diaphragm valve member 142 that moves vertically to either open or close the oval tubes 126 from the remaining passages of the respirator system 100. Specifically, a spring 144 located in spring cavity 142B biases the valve member 142 upwards against a circular lip 128A at the top of the bottom tubular portion 128. This closes off the oval tube 126 to duct 130. However, when the cartridge 106 is inserted, it presses down on the two curved walls 142, thereby depressing the valve member 142 and opening the cartridge 106 to the duct 130. In this respect, the remaining portions of the respirator system 100 can be closed or isolated when swapping out used cartridges 106 for new cartridges 106.

Figure 7:
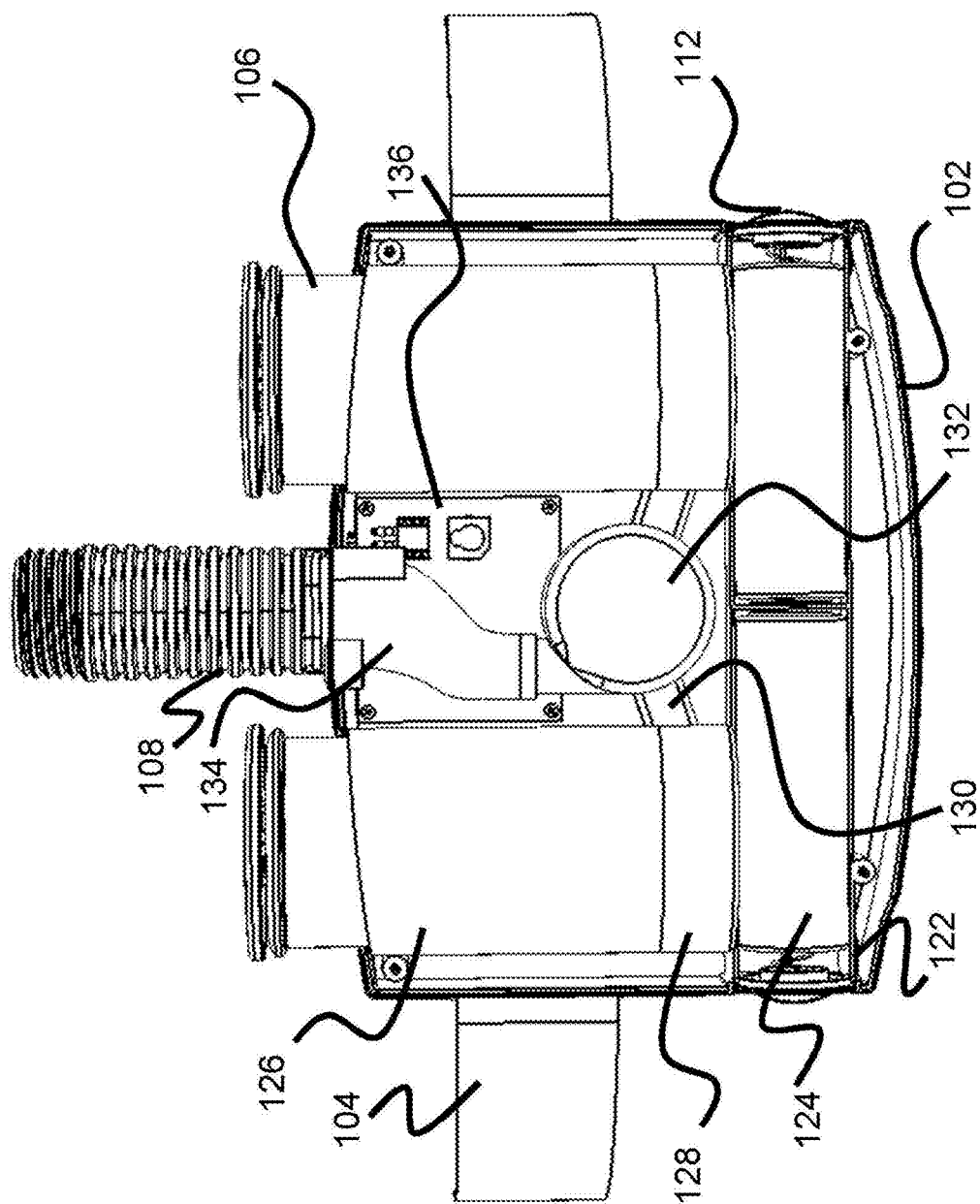
FIG. 7 illustrates an interior of a respirator system according to the present invention.
Figure 8:
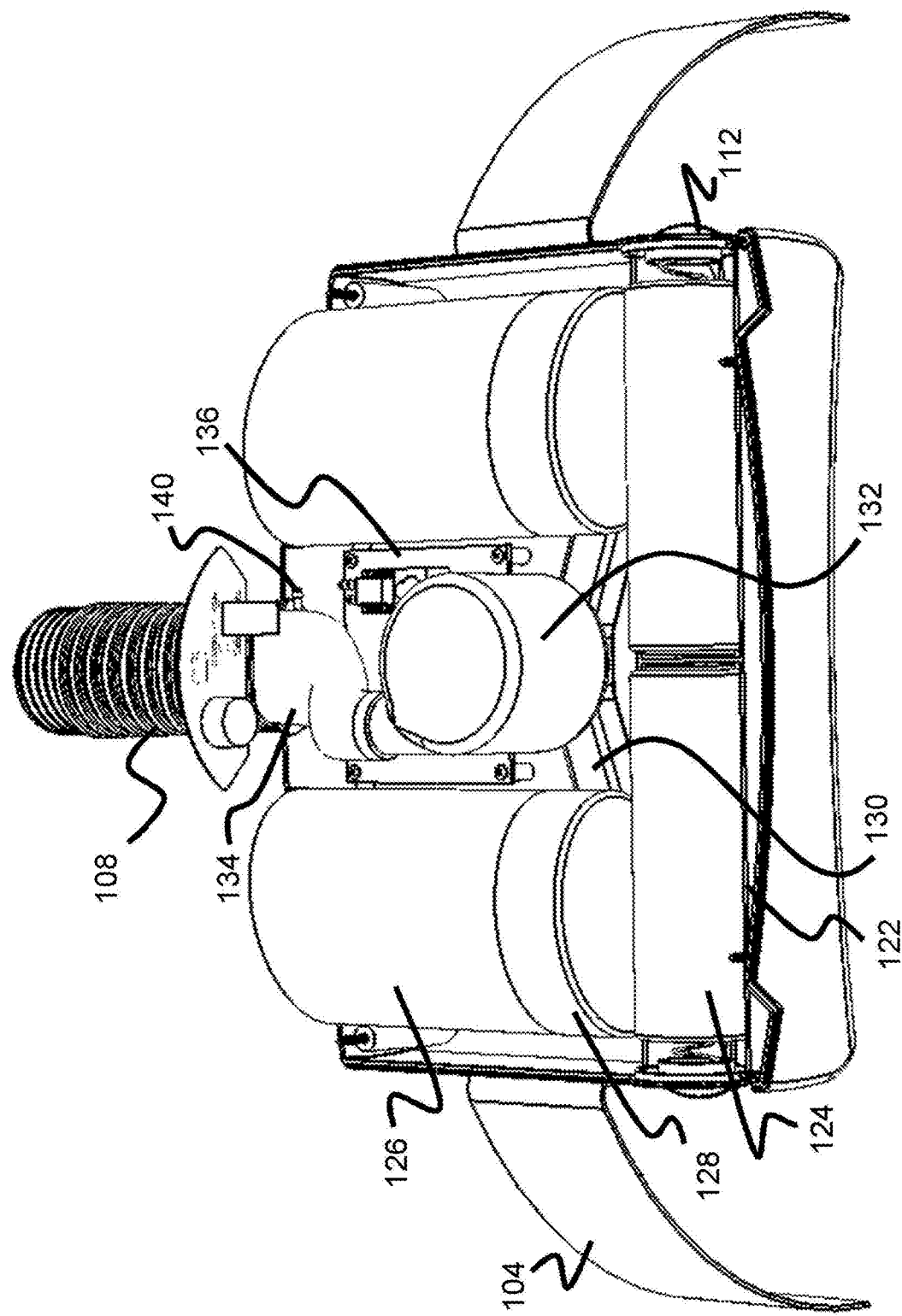
FIG. 8 illustrates an interior of a respirator system according to the present invention.
Figure 9:
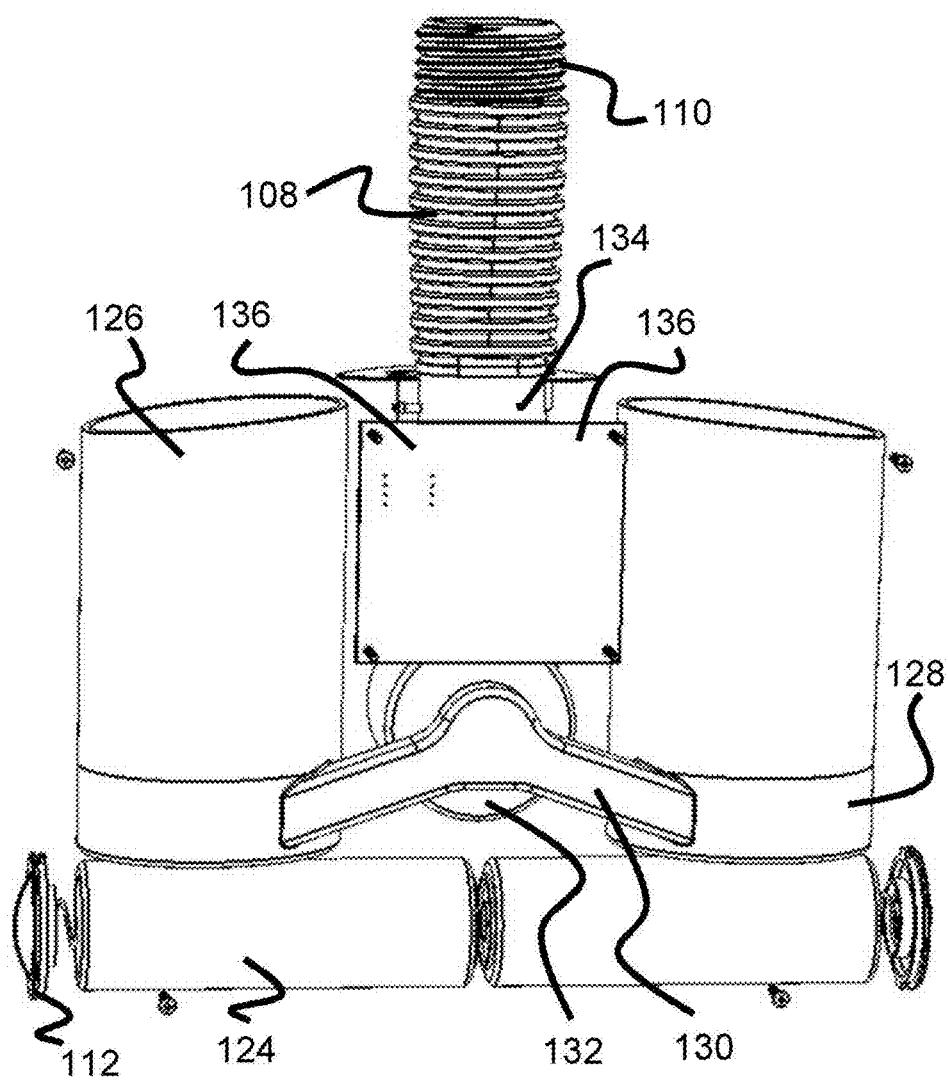
FIG. 9 illustrates an interior of a respirator system according to the present invention.

The ducts 130 connect to a two-stage centrifugal fan 132, as best seen in FIGS. 7-9. In one embodiment, the two-stage centrifugal fan 132 comprises two sets of fan blades that are axially aligned with each other and that both rotate. An additional set of non-rotating fan blades may also be included between the two rotating sets of fan blades. This two-stage design allows for high efficiency and higher air pressures/flow at slower motor speeds. Additionally, this design allows for a smaller fan/blower design than would otherwise be needed for a single-stage fan. For example, the fan may be about 2×2×2.5 inches and still provide the desired amount of flow and pressure.

Figure 19:
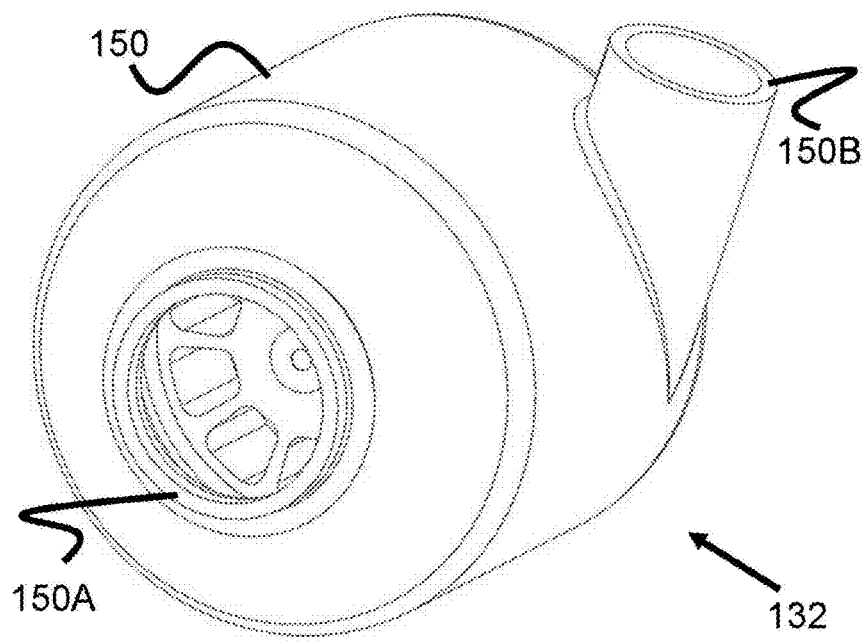
FIG. 19 illustrates a perspective view of a dual stage fan blower according to the present invention.
Figure 20:
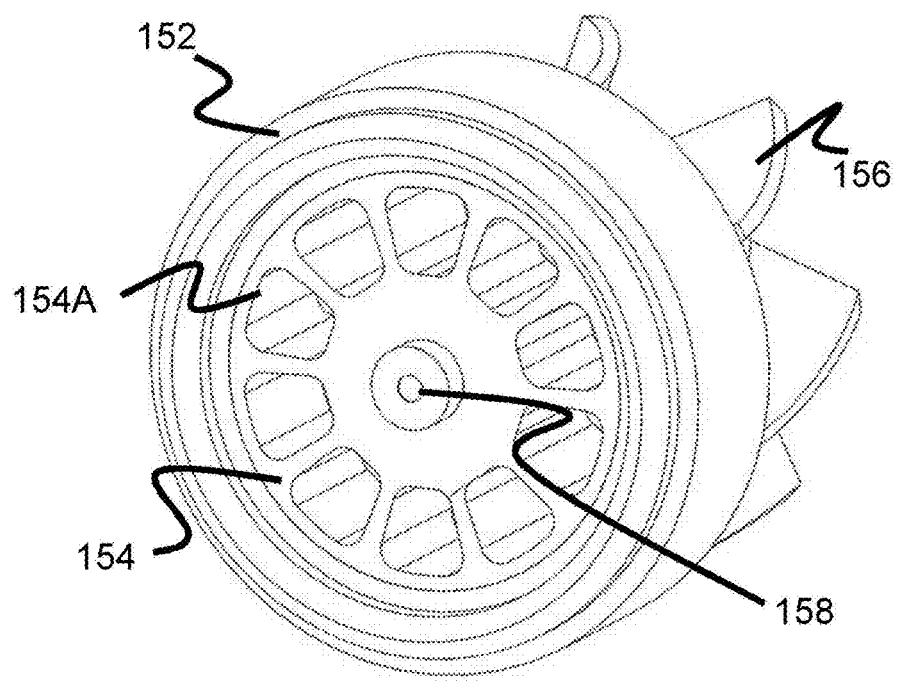
FIG. 20 illustrates an interior view of a dual stage fan blower according to the present invention.
Figure 21:
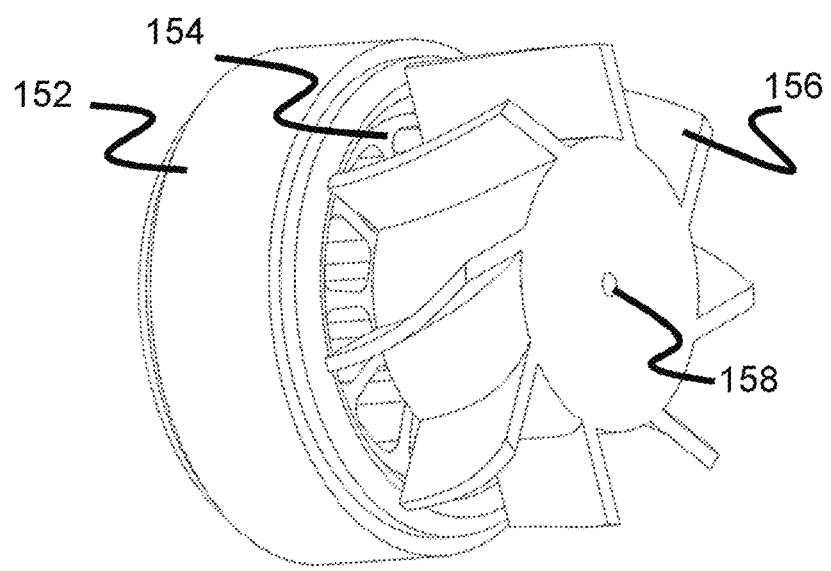
FIG. 21 illustrates an interior view of a dual stage fan blower according to the present invention.

FIGS. 19-21 illustrate one specific example design of the two-stage fan 132 that includes an outer housing 150 having an inlet 150A and an outlet 152B. fixed within the housing 150 is a stator 152 having electromagnetic windings that are connected to a fan driver on the circuit board 136 to selectively supply power thereto. Within the circular or tubular stator 152 is a disc 154 having permanent magnets embedded within its periphery and a plurality of apertures 154A positioned at intervals radially around the disc 154. Preferably, the apertures 154A extend in a relatively straight trajectory through the disc 154 (i.e., their walls are generally perpendicular to the face of the disc 154). The disc 154 is fixed to axle 158, which is mounted within the housing 150 to rotate. The axle 158 is further connected to fan 156 which comprises a plurality of fan fins fixed to the axle 158. In this respect, when the windings of the stator are powered, they create a magnetic field that interacts with the permanent magnets in the disc 154, causing it and the axle 158 to rotate. Since the fan 156 is fixed to the axle 158, it also rotates. In this regard, the fins of the fan 156 and the apertures 154A of the disc 154 rotate in a dual stage manner.

The fan 132 blows the air into the vertical, internal duct 134, which then passes into the adapter tube 108 and finally into the tube of the gas mask or hood attached to the connector 110. In this regard, clean air is provided to the user.

As best seen in FIGS. 7-9, the respirator system 100 includes a printed circuit board 136, which includes a number of different electronic components that operate the system. Specifically, the circuit board 136 includes a microprocessor or microcontroller that executes firmware and/or software, memory for storing such firmware/software, sensors, and connections to the power button 118 and LED indicators (e.g., lower battery, low pressure, and change filter).

One sensor on the printed circuit board 136 is used to determine the respiration rate of the user wearing the attached mask or hood, which in turn, allows the microcontroller to adjust the speed of the two-stage centrifugal fan 132 to an appropriate level. Hence, instead of providing the user with a maximum amount of filtered air at all times, the fan speed can be lowered to provide only the necessary amount of air. By allowing for lowered and/or variable fan speed, the battery life of the respirator system can be greatly extended.

Figure 10:
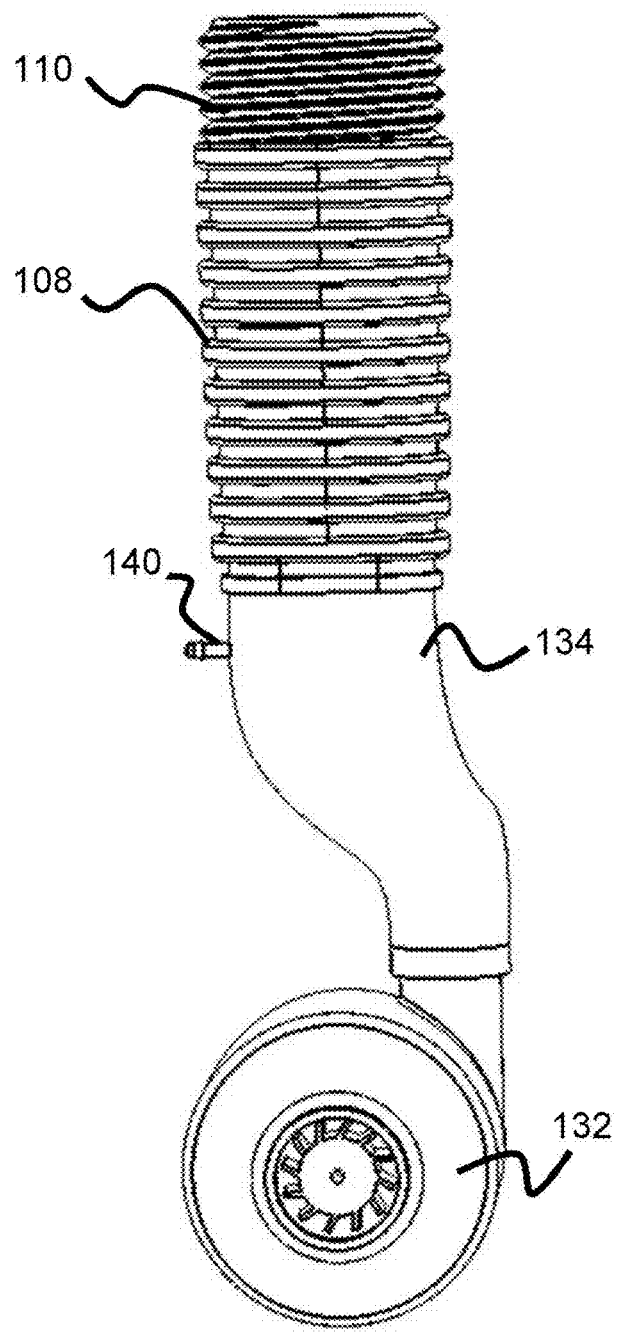
FIG. 10 illustrates a fan and ducts of a respirator system according to the present invention.
Figure 11:
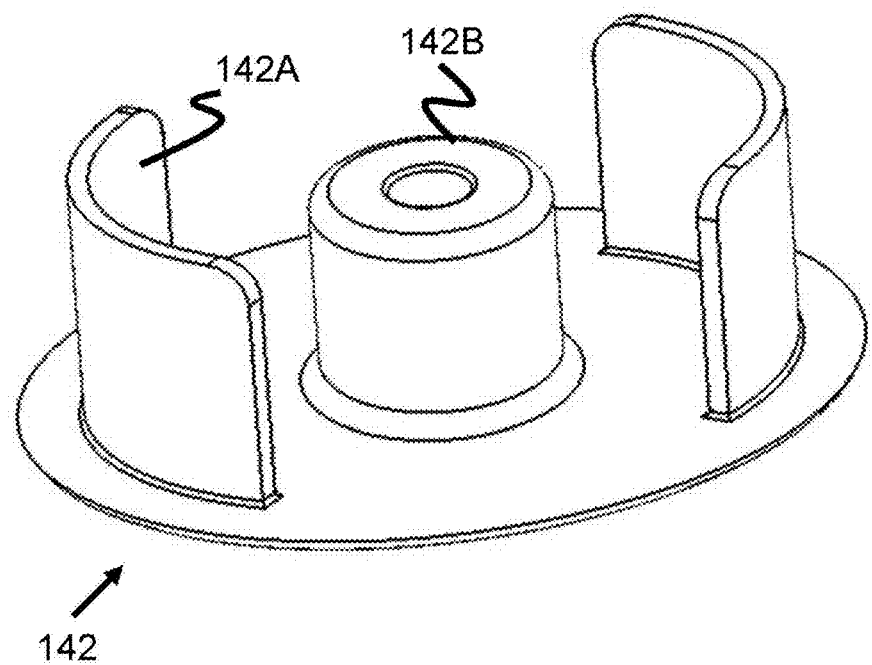
FIG. 11 illustrates a valve member of a respirator system according to the present invention.
Figure 12:
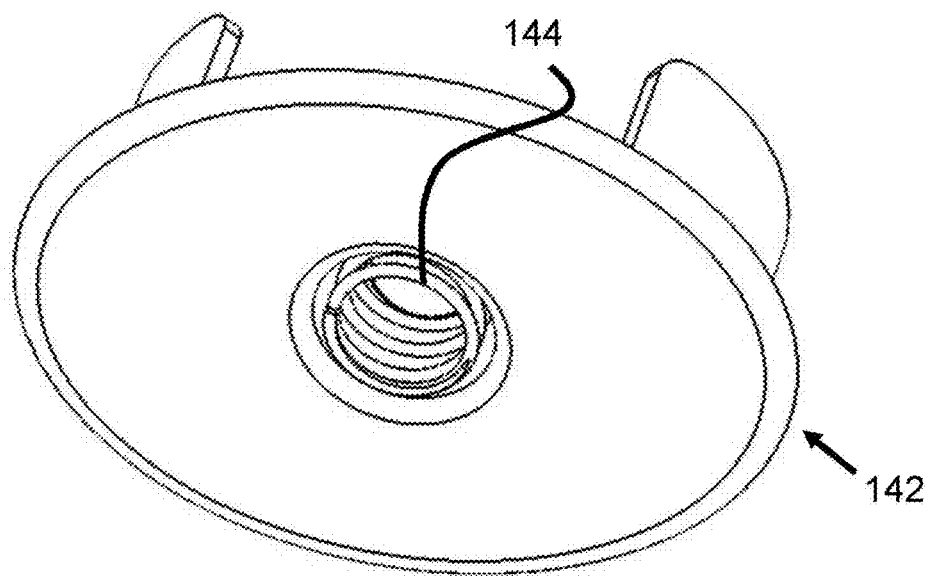
FIG. 12 illustrates a valve member of a respirator system according to the present invention.
Figure 13:
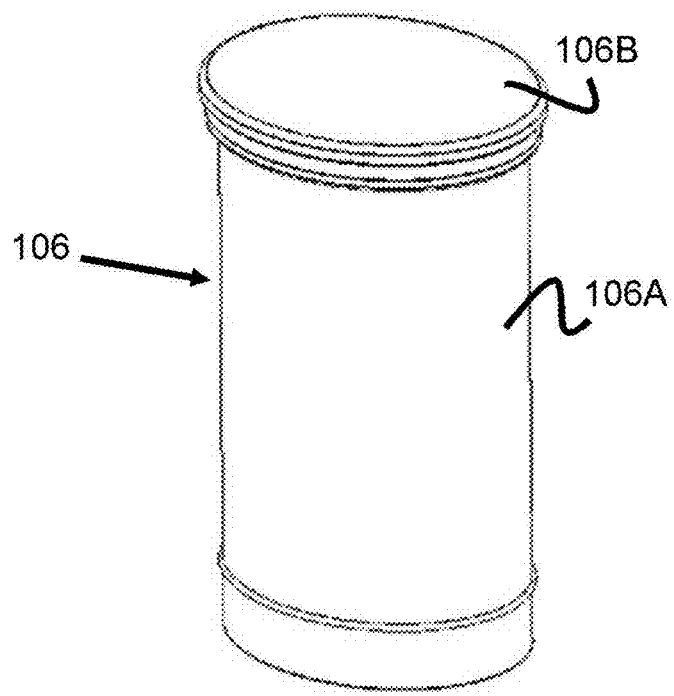
FIG. 13 illustrates a filter cartridge of a respirator system according to the present invention.
Figure 14:
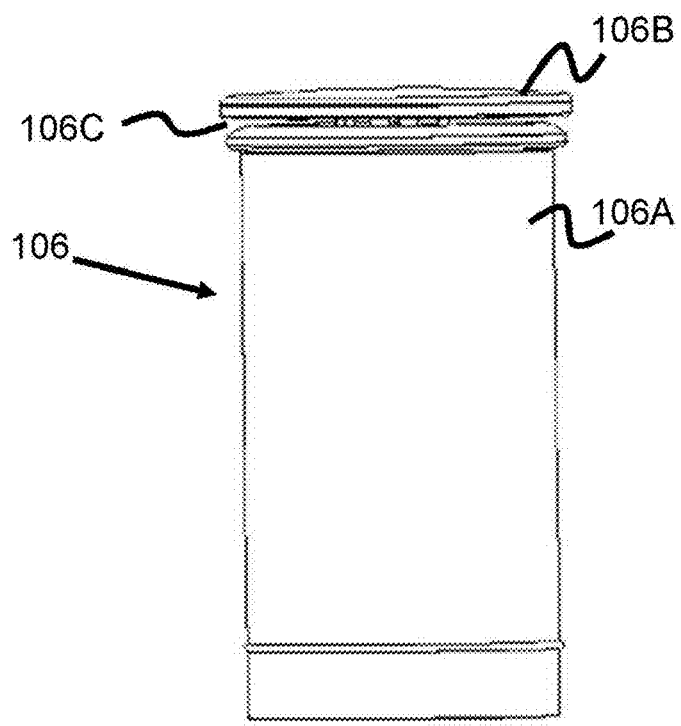
FIG. 14 illustrates a filter cartridge of a respirator system according to the present invention.
Figure 15:
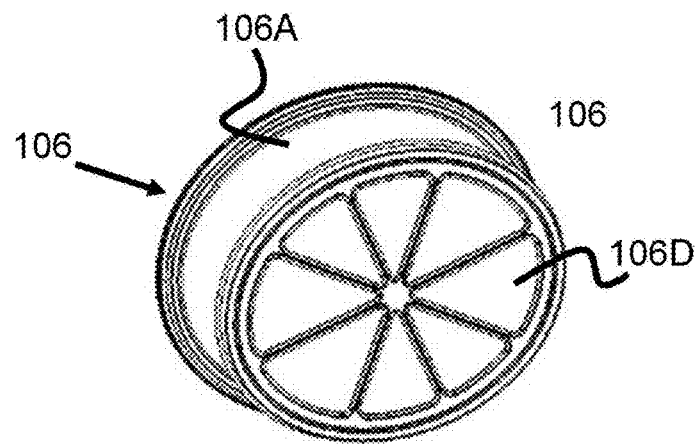
FIG. 15 illustrates a bottom view of a filter cartridge of a respirator system according to the present invention.
Figure 16:
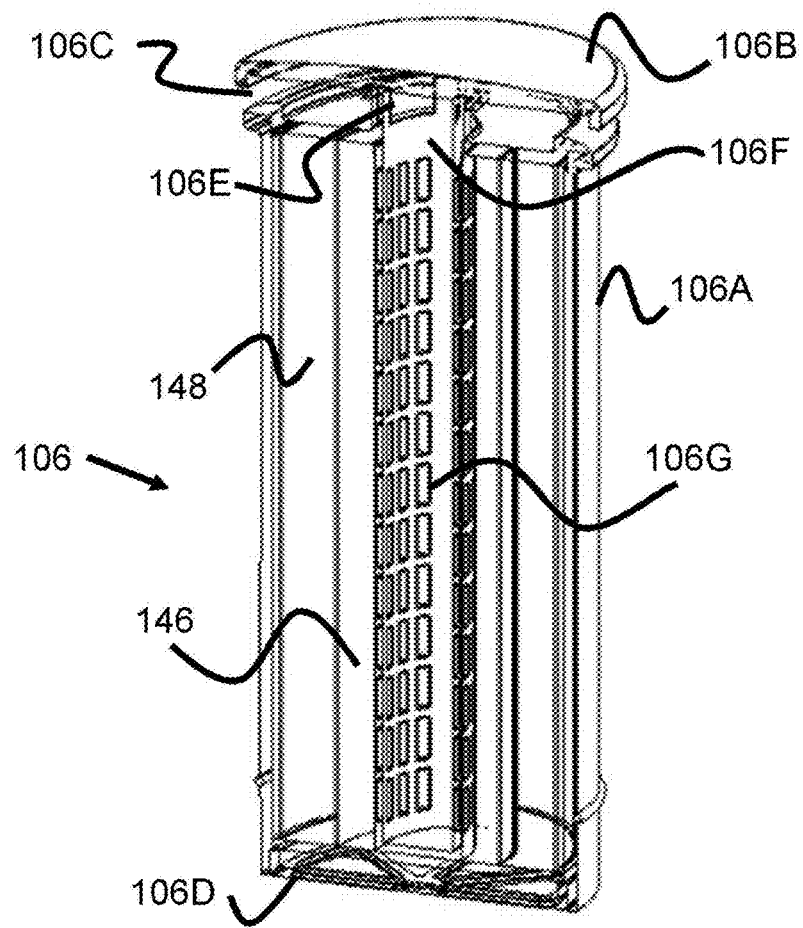
FIG. 16 illustrates a cross sectional view of a filter cartridge of a respirator system according to the present invention.
Figure 17:
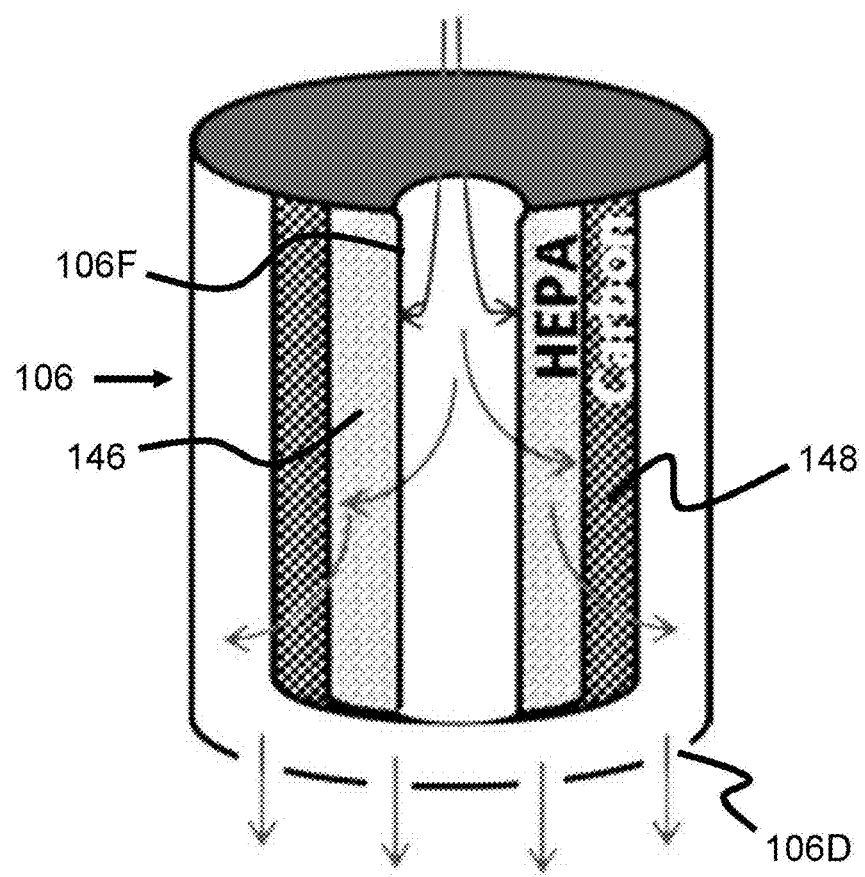
FIG. 17 illustrates air flow paths through a filter cartridge of a respirator system according to the present invention.
Figure 18:
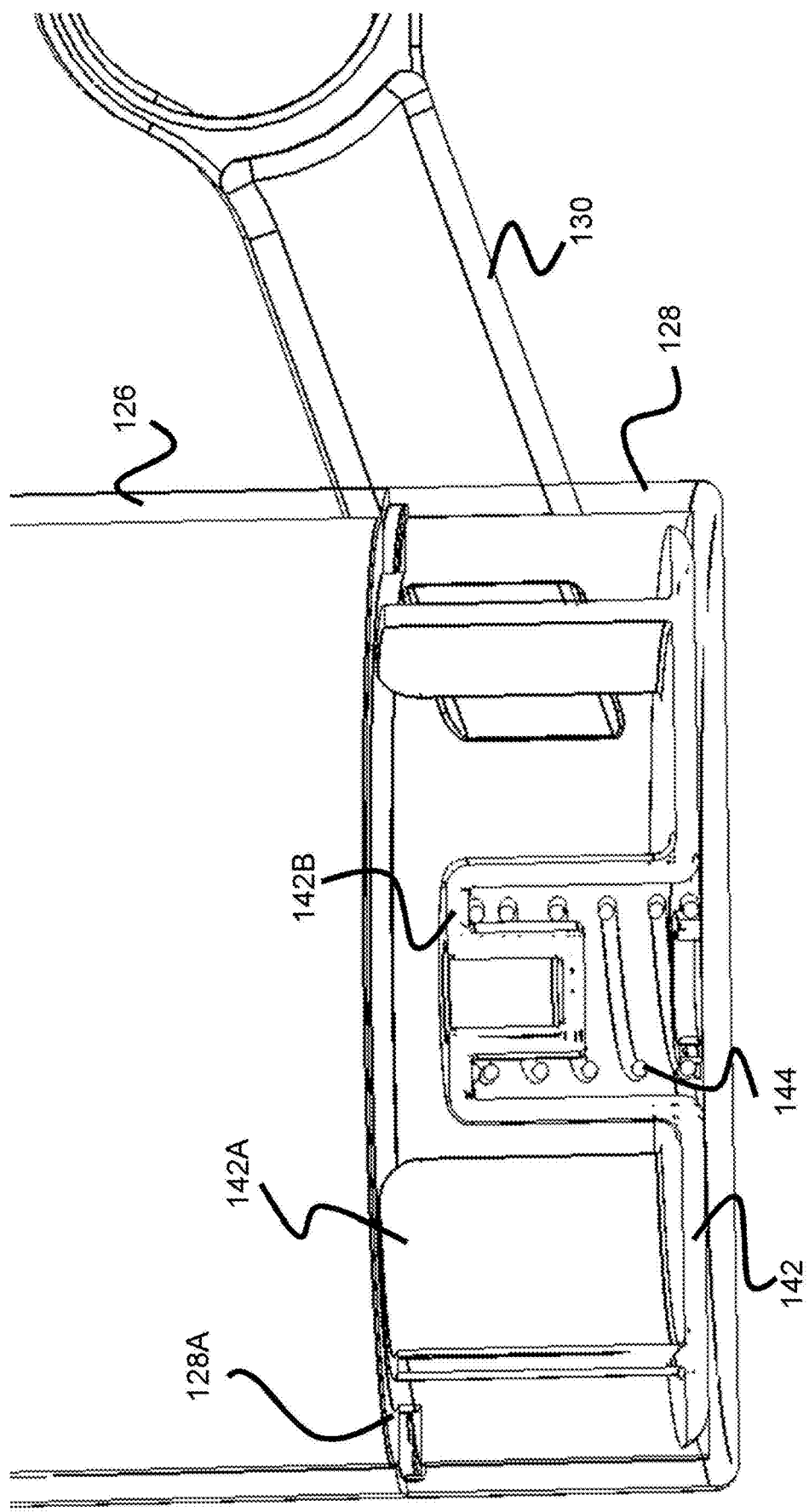
FIG. 18 illustrates a valve and duct of a respirator system according to the present invention.

In one embodiment, internal ducts 134 includes a small opening or side passage 140, as seen best in FIG. 10. This passage 140 can be connected to a tube that couples to a sensor on the printed circuit board 136, thereby placing the sensor in communication with the air in the ducts 134. Several different sensors can be used to determine or estimate the respiration rate of the user. For example, a differential air pressure sensor can be used to measure increases and decreases in air pressure in the system relative to outside, ambient air. As pressure increases, the microcontroller may determine that the user has exhaled and when pressure decreases, the microcontroller may determine that the user has inhaled. Additionally, the length, frequency, and amount of the pressure increase/decrease can also be factored into the respiration calculations (e.g., the length, frequency, and volume of the breath). Further, if the pressure within the mask/hood becomes too low, the low-pressure indicator light (FIG. 5) can be activated to alert the user. Alternately, the sensor may be a flow rate sensor that monitors the rate of air flow to estimate a respiration rate (e.g., as airflow increases, respiration can be estimated to increase). Alternately, the sensor may be an oxygen sensor or a carbon dioxide sensor that allows the microcontroller to monitor and adjust the speed of the fan 132 to maintain appropriate levels.

The side passage 140 and its connected tube can additionally be connected to other sensors. For example, a chemical sensor can be included on the printed circuit board 136, allowing the microcontroller to monitor if the filter cartridges 106 are sufficiently removing the chemicals, biological agents, or other harmful matter in the air. If the sensor detects harmful components, the microcontroller can activate the filter indicator light (FIG. 5) to alert the user. Examples of such sensors can be found in U.S. Pub. No. 2014/00046181, entitled System and Method for Chemical and/or Biological Detection, the contents of which are hereby incorporated by reference.

The printed circuit board 136 may further include an atmospheric air pressure sensor, open to ambient air pressure (not the user's purified air). The microcontroller can monitor the ambient air pressure and thereby estimate the user's elevation. Since higher elevations contain less oxygen, the speed of the fan 132 can be further increased or decreased to provide a desired amount of oxygen to the user.

As best seen in FIGS. 6-9, power is supplied to the components on the circuit board 136, as well as the fan 132, via two batteries 124. Screw open covers 112 on each side of the housing 102 can be removed to access the battery compartment 122. Preferably, the battery compartment is divided into two areas; one for each battery 124, that can each be separately accessed. This allows one of the batteries 124 to be changed out during operation of the respirator system 100 without the need to turn off the system (i.e., hot swappable). In this regard, one battery 124 is sufficient to operate the respirator system 100.

Figure 22:
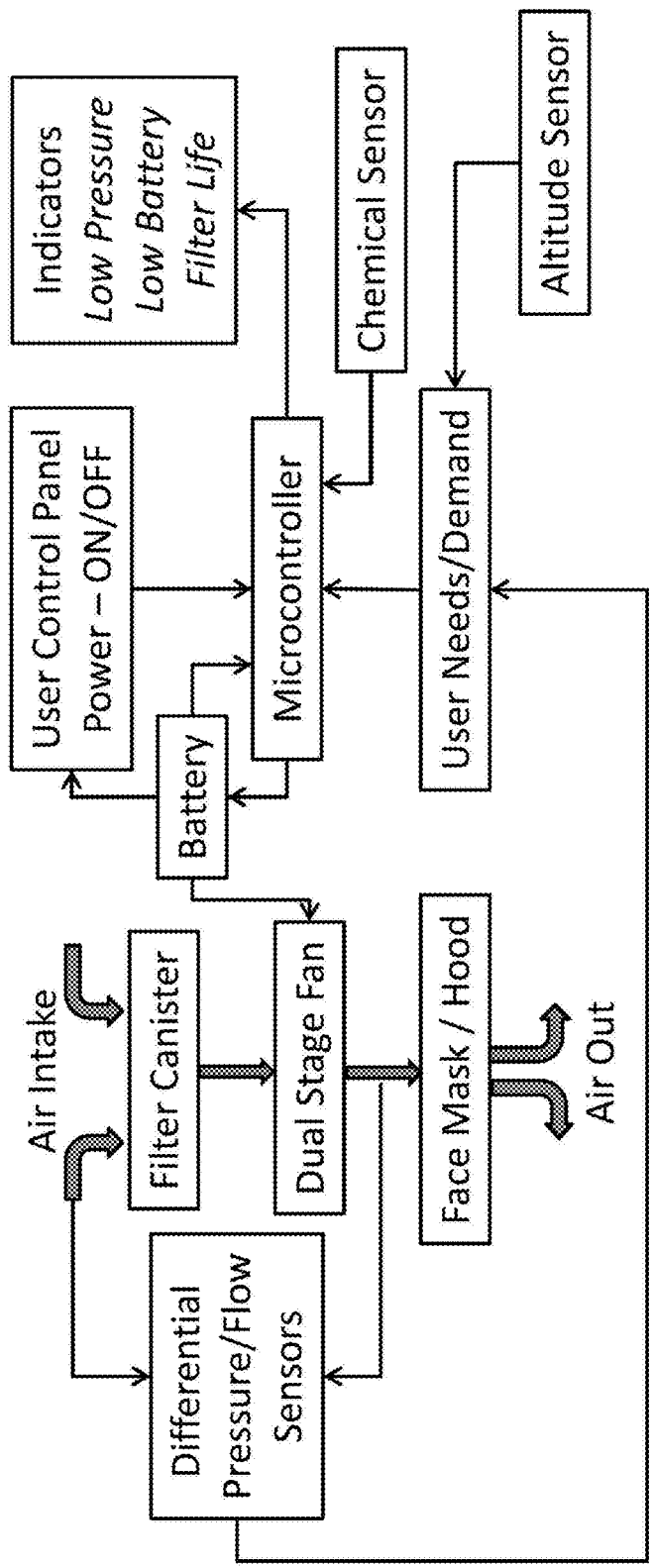
FIG. 22 illustrates a plan view of a respirator system according to the present invention.

FIG. 22 illustrates a diagrammatic functional overview of the respirator system 100. The dual stage fan 132 sucks outside air in through the filter canisters 106 and then push the filtered air on to the user's mask or hood, where excess air escapes. A differential pressure sensor (and/or a flow rate sensor) measures the pressure (or air flow) within the passages after the dual stage fan 132 and in the ambient environment to estimate the user's rate of respiration. The microcontroller monitors the estimated rate of respiration, as well as the estimated altitude and its estimated amount of oxygen to calculate a user's filtered air flow need. The microcontroller adjusts the van 132 via a fan controller to the appropriate air flow level. The microcontroller further monitors the battery level, filter life, and for low pressure within the user's mask and operates their respective indicators when problem levels arise. The battery supplies power to the microcontroller, power on/off button, and the dual stage fan 132.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An air filtering respirator, comprising:
a respirator housing;
a first area within said respirator housing that is configured to receive a first filter cartridge; said first area having an elongated vertical shape with a first opening on a top surface of said respirator housing, and a first valve mechanism at a bottom of said first area;
a second area within said respirator housing that is configured to receive a second filter cartridge; said second area having an elongated vertical shape with a second opening on said top surface of said respirator housing, and a second valve mechanism at a bottom of said second area;
a respirator output that is connectable to a user breathing enclosure;
an air passage in communication with said first valve mechanism, said second valve mechanism, and said respirator output;
said first filter cartridge being removably positioned in said first area and said second filter cartridge being removably positioned in said second area; said first filter cartridge and said second filter cartridge each having an upper side surface forming an air inlet and a bottom surface forming an air outlet;
a fan connected to said air passage; and,
a sensor in communication with said air passage;
wherein said air filtering respirator is configured to adjust a speed of said fan based on user respiration sensed by said sensor in communication with said air passage;
wherein said air filtering respirator is configured to pull air through said inlet on said upper side surfaces of said first filter cartridge and said second filter cartridge, out said bottom surface of said first filter cartridge and said second filter cartridge, through said first valve mechanism and said second valve mechanism, into said air passage, through said fan, and out said respirator output;
wherein said air filtering respirator is configured to allow removal and replacement of one of said first filter cartridge or said second filter cartridge while continuing to provide filtered air to said respirator output.

2. The air filter respirator of claim 1, further comprising a microprocessor connected to said sensor in communication with said air passage and further configured to adjust said fan.

3. The air filter respirator of claim 2, wherein said microprocessor is further connected to an atmospheric pressure sensor and configured to estimate an altitude of said air filter respirator and further adjust said speed of said fan.

4. The air filter respirator of claim 1, wherein said fan is a dual stage fan.

5. The air filter respirator of claim 4, wherein said dual stage fan comprises a first set of fan blades and a disc having a plurality of apertures, each connected to a fan axle.

6. The air filter respirator of claim 1, further comprising a chemical sensor in communication with said air passage and configured to alert a user as to detection of chemicals in said air passage.

7. The air filter respirator of claim 1, wherein said first filter cartridge and said second filter cartridge each has 1) a cylindrical shape, 2) a central air passage having a plurality of apertures extending along a length of the central air passage; and 3) a first filter disposed radially around said central air passage.

8. The air filter respirator of claim 7, wherein said first filter cartridge and said second filter cartridge each has a second filter disposed radially around said first air filter.

9. The air filter respirator of claim 8, wherein said first air filter is a HEPA filter and said second air filter is an activated carbon bed.

10. The air filter respirator of claim 9, wherein said HEPA filter is composed of a pleated glass fiber mat, and said activated carbon bed is ASZM-TEDA with Universal First Responder carbon.

11. The air filter respirator of claim 1, wherein said first valve mechanism and said second valve mechanism each comprises a diaphragm valve member located at a bottom of each of said first area and said second area; said diaphragm valve member being configured to move vertically to cause either said first valve mechanism or said second valve mechanism to open or close.

12. The air filter respirator of claim 1, wherein said first filter cartridge and said second filter cartridge each has a closed top surface and air inlets on an upper side of said at least one filter cartridge, thereby directing rain away from entering said first filter cartridge or said second filter cartridge.

13. The air filtering respirator of claim 1, wherein said fan comprises a first set of rotating fan blades; a second set of rotating fan blades that are axially aligned with the first set of rotating fan blades; and a third set of stationary fan blades positioned between said first set of rotating fan blades and said second set of rotating fan blades.

* * * * *